US007875288B2

(12) United States Patent
Balu-Iyer et al.

(10) Patent No.: US 7,875,288 B2
(45) Date of Patent: Jan. 25, 2011

(54) METHOD FOR TREATING BLOOD COAGULATION DISORDERS

(75) Inventors: Sathy V. Balu-Iyer, Amherst, NY (US); Robert M. Straubinger, Amherst, NY (US); Razvan Miclea, Simi Valley, CA (US); Aaron Peng, Amherst, NY (US)

(73) Assignee: The Research Foundation of State University of New York, Amherst, NY (US)

( * ) Notice: Subject to any disclaimer, the term of this patent is extended or adjusted under 35 U.S.C. 154(b) by 885 days.

(21) Appl. No.: 11/731,647

(22) Filed: Mar. 30, 2007

(65) Prior Publication Data
US 2007/0275050 A1  Nov. 29, 2007

Related U.S. Application Data

(60) Provisional application No. 60/787,411, filed on Mar. 30, 2006, provisional application No. 60/787,586, filed on Mar. 30, 2006, provisional application No. 60/870,177, filed on Dec. 15, 2006.

(51) Int. Cl.
*A61K 9/127* (2006.01)
*A61K 38/00* (2006.01)

(52) U.S. Cl. ........................... 424/450; 514/2; 424/1.21

(58) Field of Classification Search ........................ None
See application file for complete search history.

(56) References Cited

U.S. PATENT DOCUMENTS

| | | | |
|---|---|---|---|
| 4,127,502 | A | 11/1978 | Li Mutti et al. |
| 4,795,806 | A | 1/1989 | Brown et al. |
| 4,920,016 | A | 4/1990 | Allen et al. |
| 5,573,779 | A * | 11/1996 | Sato et al. .................. 424/450 |
| 5,580,856 | A | 12/1996 | Prestrelski et al. |
| 6,228,613 | B1 | 5/2001 | Fischer et al. |
| 6,593,294 | B1 | 7/2003 | Baru et al. |
| 2002/0098192 | A1 | 7/2002 | Whitlow et al. |
| 2002/0132982 | A1 | 9/2002 | Balasubramanian et al. |
| 2003/0118539 | A1 | 6/2003 | Fahl et al. |
| 2003/0176331 | A1 | 9/2003 | Rosenblum et al. |
| 2004/0229793 | A1 | 11/2004 | Balasubramanian et al. |
| 2004/0229794 | A1 * | 11/2004 | Ryan et al. .................. 514/12 |
| 2006/0246124 | A1 * | 11/2006 | Pilkiewicz et al. .......... 424/450 |

FOREIGN PATENT DOCUMENTS

| | | |
|---|---|---|
| CA | 2181390 | 4/2001 |
| WO | WO99/55306 | 11/1999 |

OTHER PUBLICATIONS

Kirby, et. al., *Preparation of liposomes containing factor VIII for oral treatment of haemophilia*. Journal of Microencapsulation, Jan. 1984, vol. 1, pp. 33-45.
Aguilar, et. al., *Phospholipid membranes form specific nonbilayer molecular arrangements that are antigenic*, Sep. 1999, Journal of Biological Chemistry, vol. 274, No. 36, pp. 25193-25196.
Manning, et al., *Stability of Protein Pharmaceuticals*; Pharmaceutical Research, vol. 6, No. 11, 1989, pp. 903-918.
Balasubramanian, et al., *Liposomes as Formulation Excipients for Protein Pharmaceuticals: A Model Protein Study*; Pharmaceutical Research, vol. 17, No. 3, 2000, pp. 344-350.
Braun, et al., *Protein Aggregates Seem to Play a Key Role Among the Parameters Influencing the Antigenicity of Interferon Alpha (IFN-α) in Normal and Transgenic Mice*; Pharmaceutical Research, vol. 14, No. 10, 1997, pp. 1472-1478.
Lenting, P.J., et al., *The light chain of factor VIII comprises a binding site for low density lipoprotein receptor-related protein*; The Journal of Biological Chemistry, Aug. 1999, vol. 274, No. 34, pp. 23734-23739.
Raut, et al., *Phospholipid binding of factor VIII in different therapeutic concentrates*; British Journal of Hematology, 1999, vol. 107, pp. 323-329.
Ramani, et al.; Passive Transfer of Polyethylene glycol to Liposomal-Recombinant Human FVIII Enhances its Efficacy in a Murine Model for Hemophilia A; J. Pharm. Sciences; Feb. 2008 (e pub online); pp. 1-12.
Ramani, et al.; Phosphatidylserine Containing Liposomes Reduce Immunogenicity of Recombinant Human Factor VIII (rFVIII) in a Murine Model of Hemophilia A; J. Pharm. Sciences, Apr. 2008, vol. 97; pp. 1386-1398.

\* cited by examiner

*Primary Examiner*—Michael Burkhart
(74) *Attorney, Agent, or Firm*—Hodgson Russ LLP

(57) ABSTRACT

Provided is a method for treatment of blood coagulation disorders. The method comprises administering to an individual compositions comprising lipidic particles comprising phosphatidylcholine, phosphatidylinositol and cholesterol. One or more peptides, polypeptides or proteins involved in the blood coagulation cascade are associated with the lipidic particles.

16 Claims, 5 Drawing Sheets

METHOD FOR TREATING BLOOD COAGULATION DISORDERS

This application claims priority to U.S. Provisional application No. 60/787,411 filed on Mar. 30, 2006, U.S. Provisional application on 60/787,586, filed on Mar. 30, 2006, and U.S. Provisional application No. 60/870,177, filed on Dec. 15, 2006, the disclosures of which is incorporated herein by reference.

This work was supported by funding from the National Heart Lung and Blood Institute/National Institutes of Health Grant No. HL-70227. The Government has certain rights in the invention.

BACKGROUND OF THE INVENTION

In the treatment of diseased conditions, therapeutic interventions are often undertaken which involve administration of foreign molecules having therapeutically beneficial effects. However, such administrations can often result in unwanted side effects resulting from activation of the body's immune response. Formation of antibodies following administration of therapeutics poses a serious clinical challenge. The antibodies can abrogate activity and/or alter pharmacokinetics of the therapeutic molecules.

Hemophilia A is an inherited bleeding disorder characterized by the deficiency or dysfunction of factor VIII (FVIII). FVIII serves as a critical cofactor in the intrinsic pathway of the coagulation cascade. Replacement therapy with recombinant human FVIII (rFVIII) or plasma-derived FVIII is the most common therapy employed in controlling bleeding episodes. However, the induction of neutralizing antibodies against the administered protein in approximately 15-30% of patients is a major complication in therapy [1-3]. The neutralizing antibodies frequently target the C2 domain, which is also involved in binding to phospholipids in vivo.

FVIII is a large multi-domain glycoprotein consisting of domains A1, A2, B, A3, C1 and C2. Systematic epitope mapping studies have revealed that anti-FVIII antibodies are mainly target defined regions in the A2 (heavy chain), A3 and C2 domains (light chain) of FVIII.

Another therapeutic molecule is Factor VIIa (FVIIa). This is a trypsin-like serine protease which plays an important role in activating the extrinsic coagulation cascade. FVIIa is a poorly catalytic form of factor VII after the activating cleavage between Arg152 and Ile153. Upon injury, circulating FVIIa becomes an efficient catalyst when forming a complex with tissue factor (TF), its allosteric regulator that is found on the outside of blood vessel. FVIIa-TF complex induces generation of small amounts of thrombin which further triggers blood clotting. Factor VIIa has been approved by the Food and Drug Administration in the United States for uncontrollable bleeding in hemophilia A and B patients who have developed inhibitory antibodies against replacement coagulation factors, factor VIII and factor IX. Intravenous administration of recombinant human Factor FVIIa (rHu-FVIIa) has been introduced because of fewer side effects than other alternative treatment strategies and to circumvent difficulty in preparing plasma-derived FVIIa. However, the short circulation half-life of FVIIa requiring repeated bolus injections to achieve desired efficacy can be problematic.

Additionally, other proteins involved in the blood coagulation cascade can also be used as therapeutics. Strategies that can inhibit processing by immune system and also prolong circulation time (reduce frequency of administration) would improve efficacy of therapeutic proteins. Therefore there is a need in the area of therapeutics to develop formulations that make the proteins less immunogenic, without affecting the circulating time or the efficacy.

SUMMARY OF THE INVENTION

The present invention provides a method for treating blood coagulation disorders. The method comprises administering to an individual in need, compositions comprising therapeutic agents associated with lipidic particles comprising phosphatidylcholine (PC), phosphatidylinositol (PI) and cholesterol such that the immunogenicity of the agents is reduced and/or their circulating time is increased. The therapeutic agents used for treatment of blood coagulation disorders (such as hemophilia) are peptides, polypeptides and/or proteins involved in the blood coagulation cascade or their functional truncated fragments including proteins such as Factor VIII (FVIII), B domain deleted Factor VIII (BDDFVIII), Factor VII (FVII), Factor V (FV), Factor IX (FIX), von Willebrand Factor (vWF), von Heldebrant factor (vHF) and the like.

BRIEF DESCRIPTION OF THE DRAWINGS

In the description, the therapeutic agent associated with the lipidic particles comprising PI is sometimes referred to as therapeutic agent-PI.

DESCRIPTION OF THE INVENTION

The present invention provides methods and compositions for less immunogenic and long circulating lipidic formulations for delivering a therapeutic agent in the treatment of blood coagulation disorders such as hemophilia. The word "treatment" as used herein means reducing the severity of the disease. The compositions comprise a therapeutic agent associated with lipidic structures comprising phosphatidyl choline (PC), and phosphatidyl inositol (PI) and cholesterol. The therapeutic agent may be a peptide (generally 50 amino acids or less) a polypeptide (generally 100 amino acids or less) or proteins (larger than 100 amino acids) involved in the blood coagulation cascade or their functional truncated fragments including proteins such as Factor VIII (FVIII), B domain deleted Factor VIII (BDDFVIII), Factor VII (FVII), Factor V (FV), Factor IX (FIX), von Willebrand Factor (vWF), von Heldebrant factor (vHF) and the like.

Figure 1:
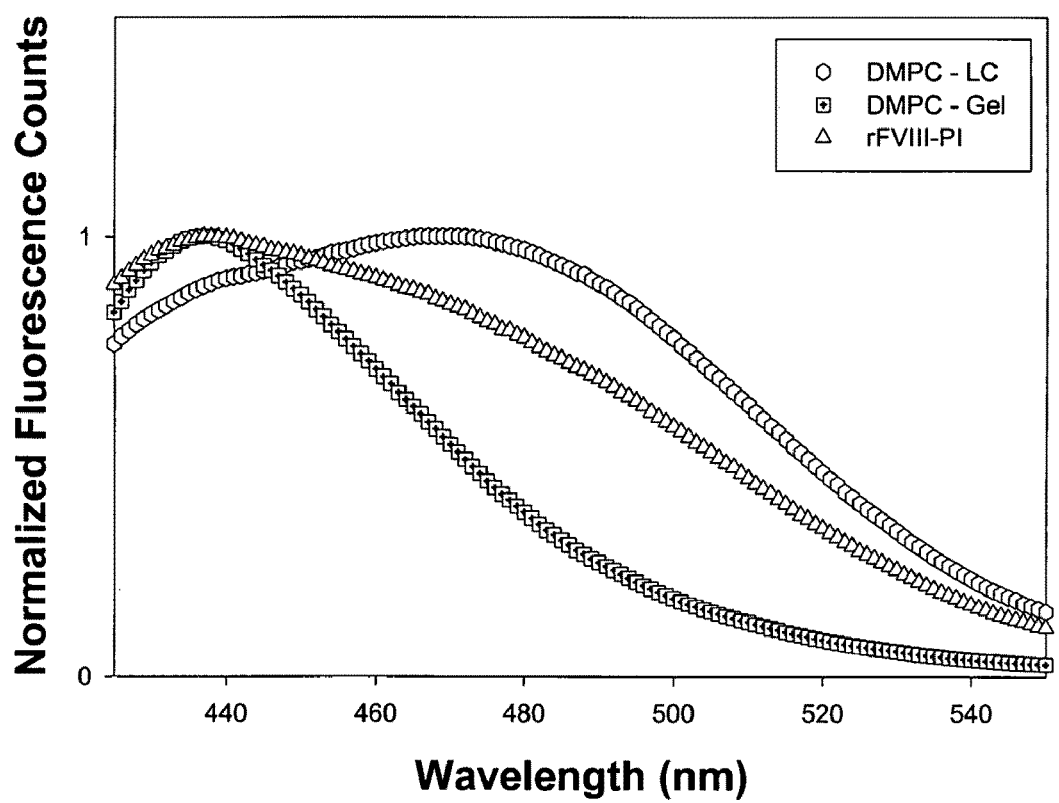
FIG. 1 is a representation of biophysical and biochemical characterization of Laurdan study of PC containing liposomes alone as a liquid or gel or PI containing lipidic particles with associated rFVIII.

Although not intending to be bound by any particular theory, it is considered that the lower imunigenicity and/or the longer circulation time is at least in part due to the lipidic particles having a unique structure. As seen under high magnification, the lipidic structures of the present invention do not appear to have donut like structures typical of liposomal lamellarity. Substantial number of the lipidic particles displayed disc like structures (see Example 2) which is attributable to reduced water volume thereby providing reduced contrast in the electron micrographs. Therefore the morphology appears different from that of liposomes, possibly due to altered lipid structure and organization, and reduced internal water volume. To further investigate the lipid structure and organization we carried out fluorescence studies using Laurdan as probe. The probe partitions into the interfacial region and the emission is sensitive to the presence and dynamics of water molecules and lamellar structures of liposomes. The fluorescence emission spectra were acquired for Laurdan labeled lipid particles of the present invention and also for liposomes, the latter serving as control. For liposomes that undergo transition from gel to liquid crystalline phase a red shift in the emission maxima, from 440 nm to 490 nm is observed (FIG. 1). Based on the composition one would expect an emission spectrum corresponding to liquid crystalline phase. However, laurdan labeled lipidic particles of the present invention showed a spectrum that is neither gel like nor liquid crystalline like. Thus, the data indicates that lamellar organization in this particle is different from that of liposomes—possibly due to the water concentration and dynamics being altered in this particle. Centrifugation studies carried out in discontinous dextran gradient indicated the particle floated more readily than liposomes. Thus, the lipidic structures of the present invention appear to have altered lipid organization and dynamics, internal water volume, water concentration and/or dynamics near the head group compared to typical liposomes. In addition, the particle may be lighter than the lamellar liposomes.

The association efficiency of the proteins in the lipidic particles as well as the reduction in the immunogenicity of proteins associated with the lipidic particles comprising PI was greater than for similar compositions in which PI was replaced with PS, PA or PG. Since PI, PS, PA and PG are all anionic phospholipids, the advantage obtained by using PI was surprising. Further because one of the proteins tested, FVIII is known to bind more avidly to PS than to PI, it was surprising that the association efficiency of FVIII for PI containing lipidic structures was higher than that for PS containing liposomes.

The present invention also provides a method for preparing the lipidic structures. The lipidic structures can be prepared by thin lipid film hydration using the appropriate molar ratios of PC, PI and cholesterol in a suitable buffer. The lipids are dissolved in chloroform and the solvent is dried. The resulting multilamellar vesicles (MLVs) are extruded through the desired size filters (sizing device) under high pressure to obtain lipidic structures of the present invention. It is generally preferred that the size of the lipidic particles should be less than 140 nm (as calculated from micrographs and dynamic light scattering measurements) so that the particles are not filtered out in the Reticulo Endothelial System (RES) so as to become available for the immune system reaction. Thus it is preferred to have at least 50% of the particles to be less than 140 nm More preferably, the particles should be less than 120 nm and still more preferably between 40 and 100 nm. In various embodiments, 50, 60, 70, 80, ad 90% of the particles are less than 140 nm and more preferably between 40 and 100 nm.

To effect association of the protein with the lipidic structures, the protein in a suitable buffer is added to the lipidic structures. The free protein is then separated from the the lipidic structures by routine centrifugation methods such as density gradient centrifugations. In various embodiments, the association efficiency of the protein with the lipidic particles is at least 30, 40, 50, 55, 60, 65, 70, 75, 80, 85, 90 and 95%. It desired, the lipidic particles with the associated therapeutic agent can be lyophilized for future use.

In one embodiment, the lipidic structures of the present invention prior to association with the protein can be lyophilized and stored. When needed, the lipidic structures can be reconstituted and then used for combination with protein to effect association of the protein with the lipidic particles prior to use.

The present invention can be used for association of therapeutic agents such as proteins, polypeptides or peptides with the lipidic structures. The protein and peptides with wide biochemical properties can be loaded in the particles. The proteins may be neutral or charged (negatively or positively). Such proteins include proteins involved in the blood coagulation cascade including Factor VIII (FVIII), Factor VII (FVII), Factor IX (FIX), Factor V (FV), and von Willebrand Factor (vWF), von Heldebrant Factor, tissue plasminogen activator, VEG-F, thrombopoietin and the like.

The ratio of PC to PI to cholesterol can be between 30:70:1 to 70:30:33. Thus the ratio of PC to PI can vary between 30:70 to 70:30. In one embodiment, it is between 40:60: to 60:40 and in another embodiment 45:55 to 55:45. In another embodiment, it is 50:50. The cholesterol (as a percentage of PC and PI together) is between 1 and 33% as structures formed at higher cholesterol ratio than 33% lack stability. In one embodiment, the cholesterol is 5-15%.

The association of the protein with the lipidic structures can be such that the molar ratio between the protein to lipid is between 1:200 (protein:lipid) to 1:30,000 (protein:lipid). In one embodiment it is about 1:10,000 (protein:lipid). In other embodiments, the ratio is about 1:2,000 or 1:4,000.

The phospholipids PC and PI have two acyl chains. The length of the acyl chains attached to the glycerol backbone varies in length from 12 to 22 carbon atoms. The acyl chains may be saturated or unsaturated and may be same or different lengths. Some non-limiting examples of 12-22 carbon atom saturated and unsaturated acyl chains are shown in Tables 1A and 1B:

TABLE 1A

| Symbol | Common Name | Systematic name | Structure |
|---|---|---|---|
| 12:0 | Lauric acid | dodecanoic acid | $CH_3(CH_2)_{10}COOH$ |
| 14:0 | Myristic acid | tetradecanoic acid | $CH_3(CH_2)_{12}COOH$ |
| 16:0 | Palmitic acid | hexadecanoic acid | $CH_3(CH_2)_{14}COOH$ |
| 18:0 | Stearic acid | octadecanoic acid | $CH_3(CH_2)_{16}COOH$ |
| 20:0 | Arachidic acid | eicosanoic acid | $CH_3(CH_2)_{18}COOH$ |
| 22:0 | Behenic acid | docosanoic acid | $CH_3(CH_2)_{20}COOH$ |

TABLE 1B

| Symbol | Common Name | Systematic name | Structure |
|---|---|---|---|
| 18:1 | Oleic acid | 9-Octadecenoic acid | $CH_3(CH_2)_7CH=CH(CH_2)_7COOH$ |
| 16:1 | Palmitoleic acid | 9-Hexadecenoic acid | $CH_3(CH_2)_5CH=CH(CH_2)_7COOH$ |
| 18:2 | Linoleic acid | 9,12-Octadecadienoic acid | $CH_3(CH_2)_4(CH=CHCH_2)_2(CH_2)_6COOH$ |
| 20:4 | Arachidonic acid | 5,8,11,14-Eicosatetraenoic acid | $CH_3(CH_2)_4(CH=CHCH_2)_4(CH_2)_2COOH$ |

The acyl chains attached to PC are preferably 12 to 22. These can be saturated or unsaturated and can be same or different length. The acyl chains attached to PI can be from 12 to 22 and can be saturated or unsaturated. The chains of the PC and the PI can be same or are different in length.

The PC and PI can be obtained from various sources both natural and synthetic. For example, soy PI and egg PC are available commercially. Additionally, synthetic PC and PI are also available commercially.

The compositions can be delivered by any standard route of administration such as intravenous, intramuscular, intraperitoneal, mucosal, subcutaneous, transdermal, intradermal, oral or the like. The compositions can be administered for reducing the severity of blood clotting disorders. In one embodiment, the compositions can be administered to an individual who has developed antibodies to one or more proteins of the blood clotting cascade such as to Factor VIII.

The invention is described by the following examples, which are intended to be illustrative and not restrictive in any way.

Example 1

This example describes the preparation of the lipidic particles.

Materials: Albumin free full-length rFVIII (Baxter Health Care Glendale, Calif.) was used as antigen. Advate was provided as a gift from Western New York Hemophilia foundation. Dimyristoyl phosphatidylcholine (DMPC) and soybean phosphatidylinositol (Soy PI) were purchased from Avanti Polar Lipids (Alabaster, Ala.). Cholesterol, IgG-free bovine serum albumin (BSA), and diethanolamine were purchased from Sigma (St. Louis, Mo.). Goat antimouse-Ig and antirat-Ig, alkaline phosphatase conjugates were obtained from Southern Biotechnology Associates, Inc. (Birmingham, Ala.). p-Nitrophenyl phosphate disodium salt was purchased from Pierce (Rockford, Ill.). Monoclonal antibodies ESH4, ESH5, and ESH8 were purchased from American Diagnostica Inc. (Greenwich, Conn.). Monoclonal antibody N77210M was purchased from Biodesign International (Saco, Me.). Normal coagulation control plasma and FVIII-deficient plasma were purchased from Trinity Biotech (County Wicklow, Ireland). The Coamatic Factor VIII kit from DiaPharma Group (West Chester, Ohio) was used to determine the rFVIII activity in plasma samples.

Preparation of rFVIII-PI lipidic particles: The particles were prepared by thin lipid film hydration of appropriate molar ratios of DMPC, soy PI, and cholesterol (50:50:5) with Tris buffer (TB) (25 mM Tris, and 300 mM NaCl, pH=7.0). The required amount of lipids was dissolved in chloroform in a kimax tube and the solvent was dried using Buchi-R200 rotaevaporator (Fisher Scientific, N.J.). Multilamellar vesicles (MLV) were formed by vortex, mixing the lipid dispersions at 37° C. for 20 min. The resulting MLV were extruded through double polycarbonate membranes of 80 nm pore size (GE Osmonics Labstore, Minnetonka, Minn.) in a high-pressure extruder (Mico, Inc., Middleton, Wis.) at a pressure of ~250 psi and then sterile-filtered through a 0.22 μm Millex™-GP filter unit (Millipore Corporation, Bedford, Mass.). Phosphate assay was used to estimate phospholipids concentrations. Particle size was monitored using a Nicomp Model CW 380 particle size analyzer (Particle Sizing Systems, Santa Barbara, Calif.). The protein was added to the lipid particles at 37° C. and during this process $Ca^{2+}$ ion concentration was decreased from 5 mM $CaCl_2$ to 0.2 mM $CaCl_2$ in TB to ensure optimal lipid-$Ca^{2+}$ interaction and possible lipid phase change. The protein to lipid ratio was maintained at 1:10,000 for all experiments, unless stated otherwise.

Separation of Free rFVIII from rFVIII-PI: Discontinuous dextran density gradient centrifugation technique was used to separate the free protein from the lipidic particles. Briefly, 0.5 ml of incubated rFVIII-PI mixture was mixed with 1.0 ml of 20% (w/v) dextran (in $Ca^{+2}$ free TB) in a 5 ml polypropylene centrifuge tube. 3 ml of 10% (w/v) dextran was then carefully added on top of the mixture followed by 0.5 ml of $Ca^{+2}$ free TB. After centrifugation at 45,000 rpm at 4° C. for 30 min in a Beckman SW50.1 rotor, the bound protein and free lipidic particles would float to the top of the dextran band unbound rFVIII would stay at the bottom of the gradient. One-stage activated partial thromboplastin time (APTT) assay was used to estimate the protein association efficiency of rFVIII-PI. This procedure yielded an association efficiency of 72±9% and is much higher than that observed with Phosphatidyl Serine (PS) containing liposomes (45±16.8%) (Purohit, et al. *Biochim Biophys Acta* 1617, 31-38 (2003). Kemball-Cook, et al., *Thromb Res* 67, 57-71 (1992)).

Example 2

This example describes characterization studies for the lipid particles prepared in Example 1. The lipid dispersion samples for microscopic analysis were prepared by air-drying on formvar-coated grids and negatively staining them with 2% uranyl acetate for approximately 1 min. The samples were photographed using a Hitachi H500 TEM operating at 75 kV. Negatives were scanned at 300 dpi with an Agfa Duoscan T1200 scanner. The morphology of the particles determined using Transmission electron microscopic studies indicated the following. The particle size was found to be around 100 nm, consistent with dynamic light scattering studies (data not shown). The analysis of the micrograph showed that the donut like structures typical of liposomal lamellarity was not observed instead particles displayed disc like structures (FIG. 2a) and it is possible that unique lipid organization distinct from liposomes are formed that can accommodate higher mol % of FVIII.

Example 3

Figure 2:
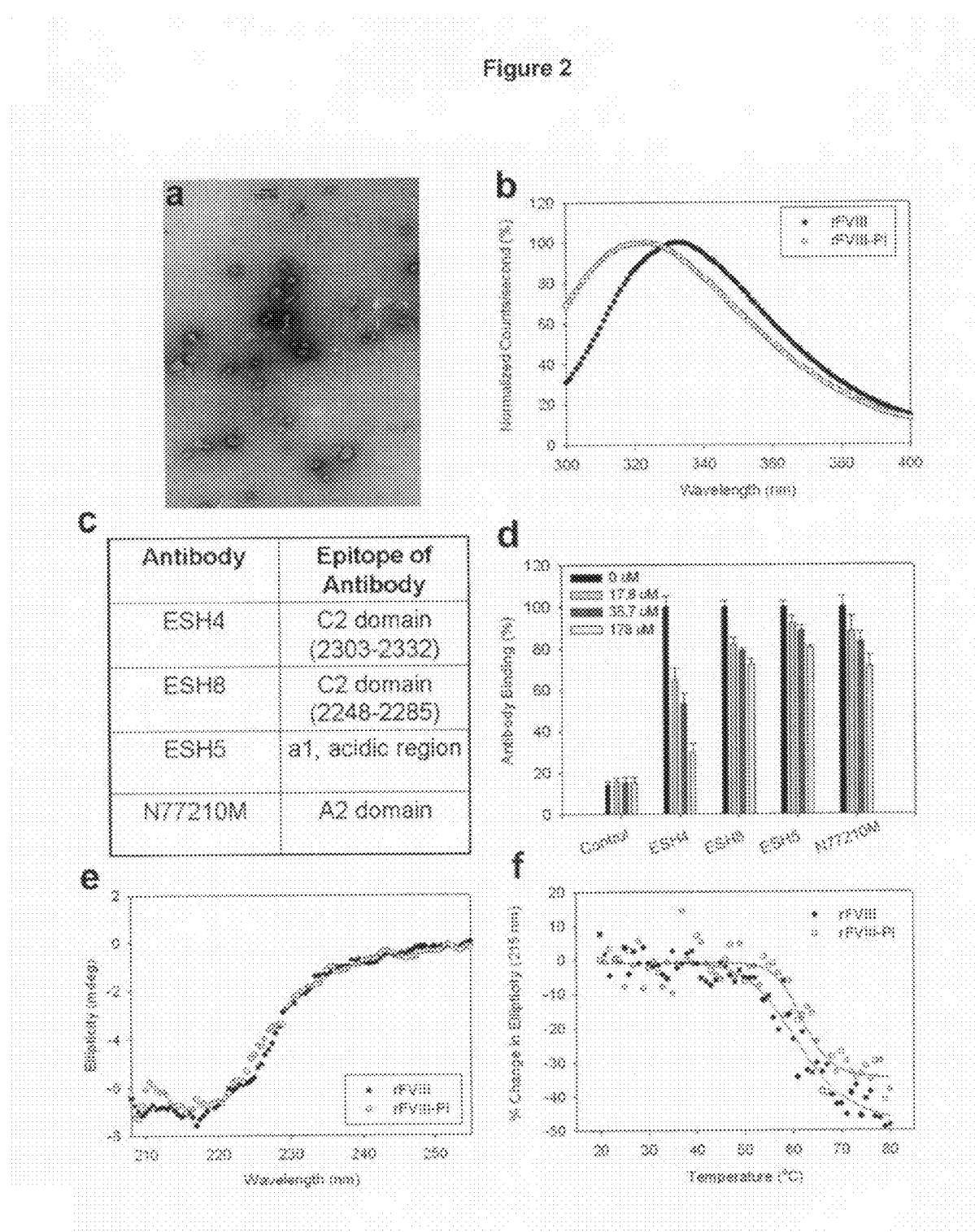
FIG. 2. Biophysical and Biochemical characterization of rFVIII-PI (a): Transmission Electron Micrograph (TEM) of rFVIII-PI; (b); normalized fluorescence emission spectra of free rFVIII and rFVIII-PI (1:10,000); (c): a list of capture monoclonal antibodies utilized in this study that target specific epitopes in rFVIII molecules; (d): the binding of monoclonal antibodies to rFVIII-PI at various lipid concentrations. Control is protein free liposomes. (e): far-UV CD spectra of rFVIII in the presence (1:2,500) and in the absence of PI acquired at 20° C.; and (f): percent change in ellipticity of rFVIII as a function of temperature in the presence and in the absence of PI.

This example describes fluorescence analysis of rFVIII and rFVIII-PI. The effect of PI on the tertiary structure of rFVIII was determined by exciting the samples either at 280 nm or at 265 nm and the emission was monitored in the wavelength range of 300-400 nm. The spectra were acquired on a PTI-Quantamaster fluorescence spectrophotometer (Photon Technology International, Lawrenceville, N.J.). Protein concentration was 5 µg/ml and slit width was set at 4 nm. The fluorescence emission spectra of FVIII loaded in this particle showed blue shifted emission maxima compared to free protein suggesting that FVIII is located in hydrophobic environment (FIG. 2b). This observation is in contrast to fluorescence spectrum observed for FVIII associated with PS containing liposomes where no change in fluorescence properties was observed (Purohit et al., 2003) and is consistent with molecular model proposed based on crystallographic and biophysical studies. FVIII was associated with PS containing liposomes only via the C-terminal region (2303-2332) of C2 domain and the rest of the molecule is accessible to bulk water (Purohit et al., 2003). However, in FVIII-PI particulates, it is likely that most of the molecular surface of FVIII is buried in hydrophobic acyl chain region of the lipidic particle and/or the protein is located at the lipid-water interface where water concentration at lipid interface may be less for PI particles.

Example 4

This example describes Sandwich ELISA and detection of rFVIII epitopes involved in rFVIII-PI association. In order to determine the rFVIII epitopes that were associated with PI, sandwich ELISAs were performed. Briefly, Nunc-Maxisorb 96-well plates were coated overnight at 4° C. with appropriate concentrations of capture monoclonal antibodies in carbonate buffer (0.2 M, pH 9.6). Plates were then washed with Tween-PBS (2.7 mM KCl, 140 mM NaCl, 1.8 mM $KH_2PO_4$, 10 mM $Na_2HPO_4.2H_2O$, 0.05% w/v Tween 20, pH 7.4) and then blocked with 1% BSA (prepared in PBS) for 2 h at room temperature. 100 µl of 0.5 µg/ml of various dilutions of rFVIII-PI (1:0, 1:5,000, 10,000, and 50,000) or PI-containing liposomes in blocking buffer were incubated at 37° C. for 1 h. Plates were washed and then incubated with 100 µl of a 1:500 dilution of rat polyclonal antibody containing a 1:1,000 dilution of goat antirat-Ig-alkaline phosphatase conjugate in blocking buffer at room temperature for 1 h. After the last wash, 200 µl of a 1 mg/ml p-nitrophenyl phosphate solution in diethanolamine buffer (1 M diethanolamine, 0.5 mM $MgCl_2$) was added and incubated for 30 min at room temperature. 100 µl of 3 N NaOH were added to stop the reaction. A plate reader was used to measure the optical density at 405 nm.

In order to investigate the molecular surface area associated with PI, sandwich ELISA studies were carried out (FIGS. 2c and 2d). The rationale for this experiment is that domains associated with lipidic particle are shielded and hence will not be available for monoclonal antibody binding. Therefore, sandwich ELISA is an indirect, qualitative method to provide insight into protein surface accessible to bulk aqueous compartment. The binding of FVIII in the absence of PI was normalized to 100% to account for differences in binding affinity of various antibodies and decrease in antibody binding in the presence of PI was interpreted as domains of FVIII involved in PI binding. PhosphatidylCholine (PC) vesicles were used as negative control as the association efficiency of FVIII in PC vesicles is around 10±4% (Purohit et al., 2003. Biochim Biophys Acta, 1617:31-38). PS liposomes were used as positive control for binding of C2 domain antibodies based on crystallographic and biophysical/biochemical studies. It has been shown that C-terminal region of the C2 domain involving 2303-2332 is involved in lipid binding and the A2 domain is further apart from the liposome surface (Stoilova-McPhie et al., 2002, Blood, 99:1215-1223). Based on this molecular topology, C2 and A2 domains are spatially well separated and only lipid-binding region in C2 domain may be shielded from antibody binding due to liposome association (Purohit et al. 2003; Stoilova-McPhie et al., 2002). Monoclonal antibodies directed against C2 and A2 domains were chosen based on this molecular model of FVIII bound to PS containing liposomes. The results indicated that the molecular surface of FVIII that is in contact with PI is different from that observed for PS. In PC liposomes no lipid concentration dependent change in antibody binding was observed indicating that no specific binding between FVIII and PC, whereas for PS vesicles, lipid concentration dependent changes observed only for antibody directed against the lipid binding domain (ESH 4), consistent with the model proposed based on crystallographic studies. However, for FVIII-PI, all the monoclonal antibodies used in this study showed reduced binding and was dependent on PI concentration (FIG. 2d). The results indicated that both C2 and A2 domains are somewhat inaccessible for antibody binding possibly due to steric hindrance and/or substantial surface area of the FVIII molecule is buried in the PI particle.

Example 5

This example describes CD analysis of rFVIII and rFVIII-PI. CD spectra were acquired on a JASCO-715 spectropolarimeter calibrated with d-10 camphor sulfonic acid. The protein to lipid ratio was 1 to 2,500 where the protein concentration used was 20 µg/ml (98.6 IU/ml). Spectra were obtained over the range of 255 to 208 nm for secondary structural analysis using a 10 mm quartz cuvette. Thermal denaturation of the rFVIII and rFVIII-PI was determined by monitoring the ellipticity at 215 nm from 20 to 80° C. using a heating rate of 60° C./h. The light scattering effect due to the presence of lipidic particles was corrected as described previously (Balasubramanian et al., 2000, *Pharm Res* 17, 344-350).

The CD studies showed that such molecular topology did not alter the secondary structure of the protein, as the CD spectrum of the protein was not changed by PI association (FIG. 2e). Thermal unfolding is often used to investigate the intrinsic stability. FVIII associated with PI nano particle displayed a shallower melting with Tm slightly higher than that observed for FVIII indicating that the association of FVIII with PI improved the intrinsic stability of FVIII (FIG. 2f).

Example 6

The association of the protein was carried out in several buffer systems as shown in Tables 2A-2C. In all the cases the protein to lipid ratio was 1:10,000. The free protein was then separated from the lipidic structures by density gradient centrifugations and the protein associated with each fraction was measured using activity and spectroscopic assay.

Table 2A shows the percentage of rFVIII associated with 50% DMPC:50% SPI:5% Chol (100 nm) with different buffer compositions at 37° C. Table 2B shows the percentage of rFVIII associated with 50% DMPC:50% SPI (100 nm) with different buffer compositions at 37° C. Table 2C: Percentage of rFVIII associated with 50% DMPC:50% SPI:15% Chol (100 nm) with different buffer compositions at 37° C.

TABLE 2A

| Buffer Composition | Percent Association |
| --- | --- |
| 300 mM NaCl, 25 mM Tris, pH 7.4 | 70~80 |
| PBS, pH 7.0 | 95 |
| 50 mM Tris, 150 mM NaCl, 3 mM NaN$_3$, pH 7.4 | 96 |
| 25 mM Tris, pH 7.4 | 42 |
| 10 mM Hepes, pH 7.4 | 23 |

TABLE 2B

| Buffer Composition | Percent Association |
| --- | --- |
| 300 mM NaCl, 25 mM Tris, pH 7.4 | 67 |
| PBS, pH 7.0 | 88 |
| 50 mM Tris, 150 mM NaCl, 3 mM NaN$_3$, pH 7.4 | 58 |
| 10 mM Hepes, pH 7.4 | 33 |

TABLE 2C

| Buffer Composition | Percent Association |
| --- | --- |
| 300 mM NaCl, 25 mM Tris, pH 7.4 | 66 |
| PBS, pH 7.0 | 93 |
| 50 mM Tris, 150 mM NaCl, 3 mM NaN$_3$, pH 7.4 | 51 |
| 10 mM Hepes, pH 7.4 | 32 |

Example 7

This example describes immunogenicity studies: Breeding pairs of hemophilia A mice (C57BL/6J) with a target deletion in exon 16 of the FVIII gene were used. A colony of hemophilia A mice was established and animals aged from 8-12 weeks were used for the in vivo studies. Since the sex of the mice has no impact on the immune response, both male and female mice were used for the studies.

The relative immunogenicity of free rFVIII and rFVIII-PI were determined in hemophilia A mice. This mouse model is suitable for investigating immunogenicity of FVIII as the antibody response patterns against FVIII are very similar to those observed in hemophilic patients. 8 male and 10 female mice received 4 weekly intravenous injections (via penile vein) and subcutaneous injections of 10 IU of FVIII (400 IU/kg), respectively. 2 weeks after the last injection, blood samples were collected in acid citrate dextrose (ACD) buffer (85 mM sodium citrate, 110 mM D-glucose and 71 mM citric acid) at a 10:1 (v/v) ratio by cardiac puncture. Plasma was separated by centrifugation at 5,000 rpm at 4° C. for 5 min. Samples were stored at −80° C. immediately after centrifugation. The total titers were determined by ELISA studies and the inhibitory titer was determined using a modified Bethesda assay as described previously (verbruggen et al., Thromb Haemost, 1995, 73:2470251).

Figure 3:
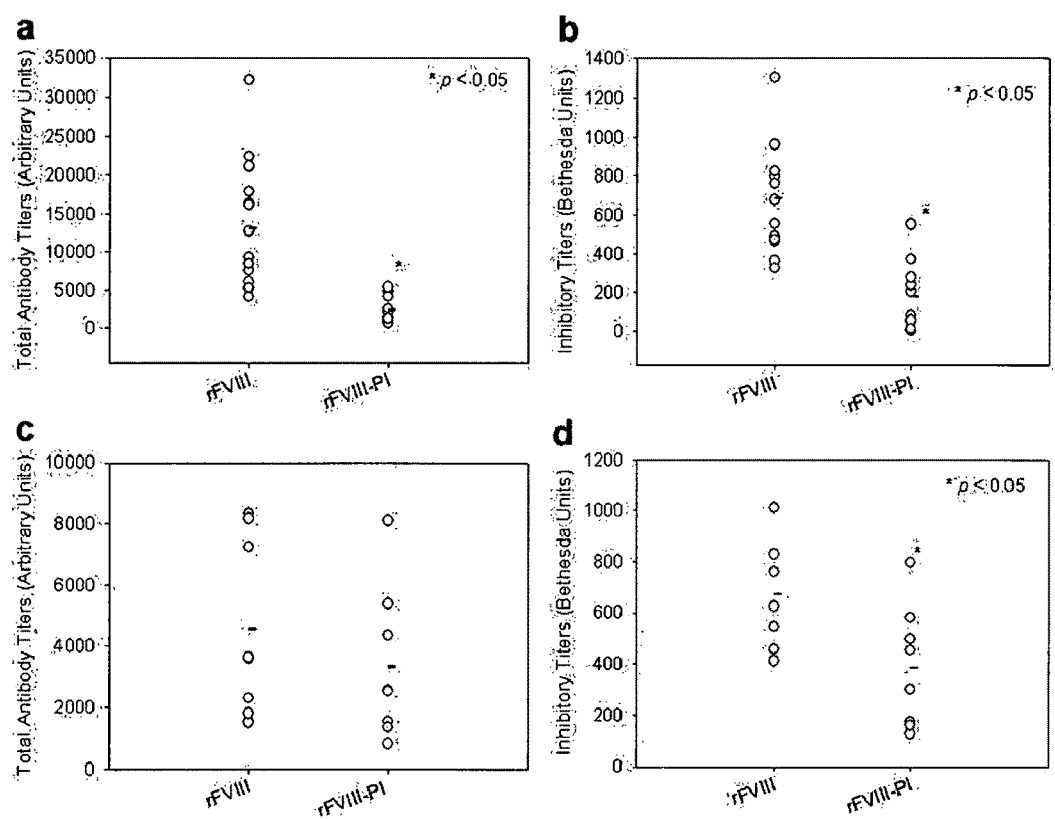
FIG. 3. Effect of phosphatidylinositol on the Immunogenicity of rFVIII. (a, c) show the mean of total antibody titers (horizontal bars) and individual (open circles) antibody titers were determined following s.c. and i.v. administrations, respectively. (b, d) show the mean of inhibitory titers (horizontal bars) and individual (open circles) inhibitory titers were determined following s.c. and i.v. administrations, respectively.
Figure 4:
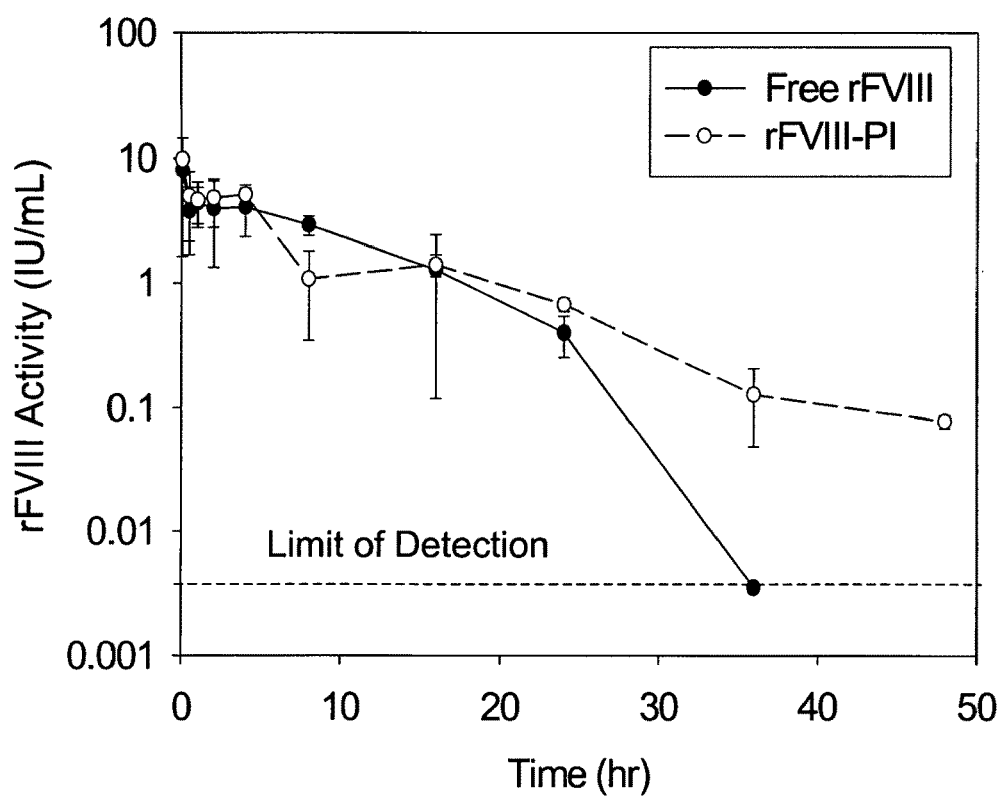
FIG. 4. Influence of phosphatidylinositol on pharmacokinetics of rFVIII. The mean plasma concentration of rFVIII clotting activity after i.v. administration of free rFVIII and rFVIII-PI.

The results showed that PI reduced antibody response in Hemophilia mice (FIG. 3). Animals treated with rFVIII-PI displayed significantly lower total antibody titers (FIGS. 3a and 3c) compared to animals treated with rFVIII alone. Titers were 2379±556 (±S.E.M; n=10) for FVIII-PI given by sc route, compared to 13,167±2042 (n=15) for animals treated with rFVIII alone. These differences were significant at P<0.05. Animals treated with rFVIII-PI by i.v. also showed lower mean antibody titers; for FVIII-PI antibody titers were found to be of 3321±874 (n=8) and those treated with rFVIII had titers of 4569±1021(n=8) and this difference was not significant. However, the inhibitory titers that abrogate the activity of the protein reduced significantly for FVIII-PI given by both sc and iv route (FIGS. 3b and 3d). For sc administration, the inhibitory titers reduced by more than 70%. For animals given FVIII alone by iv route, the inhibitory titers were 675±71 and it reduced to 385±84 for FVIII-PI and this reduction is statistically significant at p<0.05. Together these results indicate that PI containing lipidic particles not only reduced overall anti-rFVIII antibody titers, but also lowered the titer of antibodies that abrogate the activity of the protein.

Example 8

This example describes pharmacokinetics studies. Recombinant FVIII or rFVIII-PI (10 IU/25 g) was administered to male hemophilia A mice as a single intravenous bolus injection via penile vein. Blood samples were collected in syringes containing ACD buffer (10:1 v/v) at 0.08, 0.5, 1, 2, 4, 8, 16, 24, 36, and 48 h after the injections by cardiac puncture (n=3 mice/time point). Plasma was collected immediately by centrifugation (5,000 rpm, 5 min, 4° C.) and stored at −70° C. until analysis. Chromomeric assay was used to measure the activity of rFVIII in plasma samples. The average values of rFVIII activities at each time point were used to compute basic pharmacokinetic parameters (half-life, MRT and area under the plasma activity curve) using a no compartmental analysis (NCA)[20] (WinNonlin Pharsight Corporation, Mountainview, Calif.). The areas under the plasma activity (AUC) versus time curves from 0 to the last measurable activity time point were measured by log-linear trapezoidal method. The elimination rate constant (lambda z) was estimated by log-linear regression of the terminal phase concentration. The elimination half-life ($t_{1/2}$) was calculated as ln 2/lambda z and MRT was calculated from AUMC/AUC where AUMC is the area under the curve plot of the product of concentration and time versus time.

Data was analyzed by ANOVA using Minitab (Minitab Inc., State College, Pa.). Statistical difference (p<0.05) was detected by the Student independent t-test, and one-way ANOVA followed by Dunnette's post-hoc multiple comparison test. For PK studies, repeated-measures ANOVA was used to compare the profiles generated by the two treatments. Bailer-Satterthwaite method was used to compare differences in systemic exposure between the two treatments.

The MRT and AUC is found to be higher for FVIII-PI compared to FVIII and also showed prolonged terminal elimination phase. The circulation half-life of FVIII associated with PI lipidic particle (7.6 hrs) is higher than that observed for free FVIII (2.3 hrs). Substantial protein activity was detected after 48 hrs of injection for animals that are given FVIII-PI particles; in contrast no detectable FVIII activity was observed at 48 hrs in animals that received FVIII alone (FIG. 4). Further, the protein activity was detectable for only 24 hrs following administration of the PS containing liposomes (data not shown) and is due to the rapid uptake of PS liposomes by the RES. However, in the presence of PI it is possible that the cellular uptake is reduced and is consistent with the stealth like properties of PI.

Example 9

This examples describes the Association efficiency for rFVIII and a truncated version of FVIII. BDDrFVIII. The lipidic structures having FVIII or BDDrFVIII were prepared by a process as described above. The percent association for these proteins is shown below in Table 3.

TABLE 3

Percentage of rFVIII associated with lipidic particles of various compositions.

| Protein (protein:lipid) | Composition (molar ratio) | Lipidic particle Size (nm) | Temperature (° C.) | % Association |
|---|---|---|---|---|
| rFVIII (1:10,000) | DMPC:SPI (70:30) | 200 | 37 | 30.7 |
| rFVIII (1:10,000) | DMPC:SPI (70:30) | 100 | 37 | 43.9 |
| rFVIII (1:10,000) | DMPC:SPI (50:50) | 100 | 37 | 74.6 |
| rFVIII (1:10,000) | DMPC:SPI:Chol (70:30:5) | 100 | 37 | 30.4 |
| rFVIII (1:10,000) | DMPC:SPI:Chol (50:50:5) | 100 | 37 | 81.2 |
| rFVIII (1:10,000) | DMPC:SPI:Chol (50:50:5) | 100 | 20 | 61.8 |
| BDDrFVIII (1:10,000) | DMPC:SPI:Chol (50:50:5) | 100 | 37 | 59.0 |
| BDDrFVIII (1:10,000) | DMPC:SPI:Chol (50:50:5) | 100 | 20 | 44.7 |
| BDDrFVIII (1:20,000) | DMPC:SPI:Chol (50:50:5) | 100 | 37 | 65.0 |
| BDDrFVIII (1:20,000) | DMPC:SPI:Chol (50:50:5) | 100 | 20 | 61.3 |

As seen above, DMPC:SPI:Cholesterol (50:50:5) formulation showed highest association efficiency than other formulations for both rFVIII and BDDrFVIII. Cholesterol is preferably included in the formulation to increase liposome stability in plasma. Size of liposome and association temperature, and lipid concentration all play important roles in association. DMPC:SPI:Cholesterol (50:50:5) formulation surprisingly has higher association for rFVIII than BDDrFVIII even though BDDrFVIII has lower Molecular weight and size. Conformational changes as a result of the B domain deletion could be responsible for a decrease in the binding affinity of BDDrFVIII towards PI containing lipidic particles.

Pharmacokinetics Studies

Male hemophilic mice (20-24 g, 22-25 weeks old) were given 10 IU/25 g of rBDDFVIII associated with the lipidic structures (referred to as PI-BDDrFVIII) as a single i.v. bolus injection via the penile vein. Blood samples were collected 0.08, 0.5, 1, 2, 4, 8, 16, 24, 36, and 48 hr post dose by cardiac puncture (n=1/time point) and added to acid citrate dextrose (ACD) at a 10:1 (v/v) ratio. Plasma was separated by centrifugation at 5000 g for 5 min at 4° C. and stored at −70° C. until analysis. Plasma samples were analyzed for the activity of the protein by the chromogenic assay. The activities of BDDrFVIII determined at each time point were then utilized to estimate basic PK parameters (half-life, t1/2 and area under the plasma activity curve/exposure, AUAC)

Figure 5:
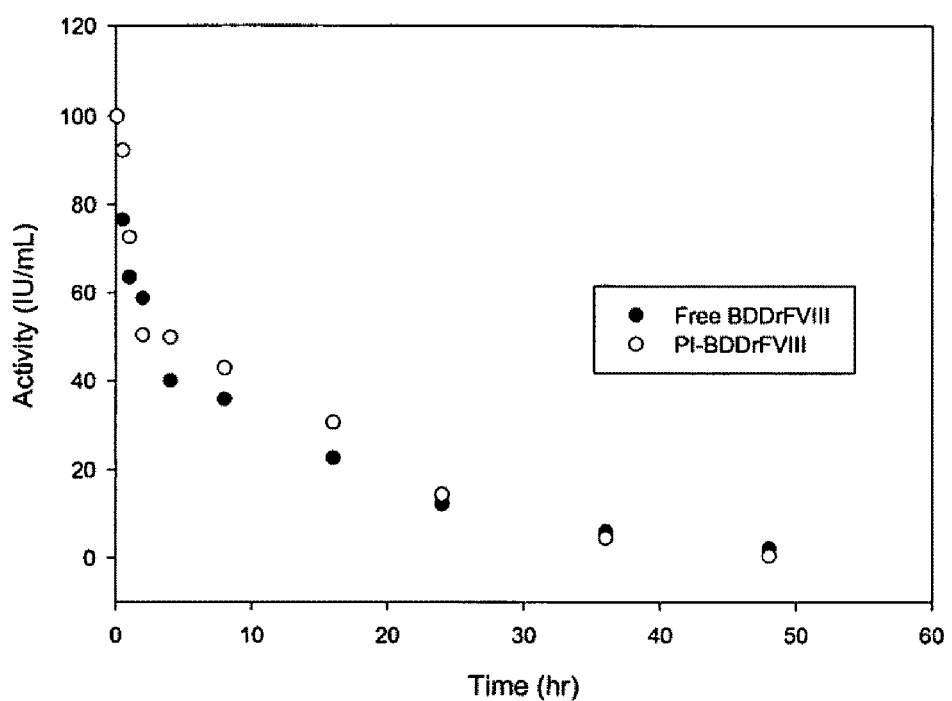
FIG. 5. Influence of phosphatidylinositol on pharmacokinetics of BDDrFVIII. The mean plasma concentration of BDDrFVIII clotting activity after i.v. administration of free BDDrFVIII and BDDrFVIII-PI.

The PK Normalized PK Profile for Free BDDrFVIII and PI-BDDrFVIII Formulation (n=1) is shown in FIG. 5. The Area Under the Curve AUC (hr*IU/mL) or Free BDDrVIII was 955.1 and for BDDFVIII associated with lipidic structures was 1058.7.

Example 10

This example describes the in vivo activity of rFVIII-PI: Tail clip method was used in hemophilia A mice to investigate rFVIII-PI activity in vivo. Animals (n=3) were administered with rFVIII alone or rFVIII-PI by intravenous route. Briefly, 2 μg (~10 IU) of rFVIII was given per 25 g of animal body weight. 48 h post the injection, tip (1 cm) of the tail was cut off using a scalpel and the survival of the animals was monitored.

In order to investigate the efficacy of FVIII-PI particle, survival experiment using tail clip method was carried out. These mice do not produce any active murine FVIII. Hence, bleeding caused due to tail clipping will result in the death of the animal in about 17 hrs as observed for sham treated animals. Thus the survival of the animal following a tail clip is a pharmaco-dynamic endpoint and indicator of efficacy. Tail of three animals that received FVIII-PI was clipped 48 hrs post injection and the survival was monitored. All three animals survived and visual examination showed that in two animals clotting was observed within 2 hrs of tail clip and in one animal it was observed around 6 hrs. The results clearly indicate that the FVIII-PI particle is efficacious and PI prolonged the circulation time of FVIII.

Example 11

This example describes the application of this method to another protein, Factor VII. In this example, lipidic structures comprising FVII were prepared. The required amounts of DMPC, SPI and Chol (Dimyristoylphosphatidylcholine (DMPC):soy phosphatidylinositol (SPI):Cholesterol (Chol) (molar ratio 50:50:5) were dissolved in chloroform. A thin lipid film was formed on the walls of a glass tube, by removing the solvent in a Buchi-R200 rotoevaporator (Fisher Scientific). The lipidic particles (LP) were prepared by rehydration of the lipid film with 25 mM tris buffer (300 mM NaCl, pH=7.0; calcium free) at 37° C. The LP were extruded twenty times through double stacked 80 nm polycarbonate membranes using a high pressure extruder (Lipex Biomembranes, Inc.) at a pressure of ~200 psi. The size distribution of the particles was monitored using a Nicomp model CW380 size analyzer (Particle Sizing System).

The association of the protein with the LP was achieved by incubating the protein in the presence of the LP at 37° C. for 30 minutes. The protein to lipid molar ratio was maintained for the first two trials of preparation (1:10,000). Additional, one trial using protein:lipid ratios of 1:2000 were also investigated To estimate the amount of protein associated with LP, free protein was separated from LP-associated protein by floatation on a discontinuous dextran density gradient. Briefly, 0.5 ml of the LP-protein mixture was mixed with 1 ml of 20% (w/v) dextran (in calcium free Tris buffer) in a 5 ml polypropylene centrifuge tube and 3 ml of 10% (w/v) dextran and 0.5 ml calcium free Tris buffer were overlaid on the LP-containing band. The gradient was subjected to ultracentrifugation at 45,000 rpm for 30 min in a Beckman SW50.1 rotor. The LP and their associated protein floated to the interface of the buffer/10% dextran bands, and the unassociated protein remained at the bottom. The concentration of the protein associated with LP was determined using spectroscopic assay. The percent association for protein:lipid of 1:10,000 was 63.9±9.6% (n=3) and the percent association for protein:lipid of 1:2,000 was 40.1±1.1% (n=3).

The invention claimed is:

1. A method of treating a blood coagulation disorder comprising administering to an individual a composition comprising lipidic particles and one or more therapeutic agents associated with the particles, wherein the lipidic particles comprise phosphatidylcholine (PC), phosphatidylinositol (PI) and cholesterol, wherein the ratio of PC to PI is between 60:40 to 40:60 and cholesterol is present between 5-15% of PC and PI together and the particles have a size of between 40 to 140 nm.

2. The method of claim 1, wherein the PC to PI ratio is between 55:45 and 45:55.

3. The method of claim 2, wherein the PC to PI ratio is 50:50.

4. The method of claim 1, wherein each acyl chains of PC and PI independently has between 12 and 22 carbon atoms, and is saturated or unsaturated.

5. The method of claim 1, wherein the PI is soy PI and the PC is egg PC.

6. The method of claim 1, wherein the therapeutic agent is selected from the group consisting of Factor VIII, Factor VII, Factor IX, Factor V, Willebrand Factor (vWF) and von Heldebrant Factor (vHF).

7. The method of claim 6, wherein the therapeutic agent in FVIII or B-domain deleted FVIII.

8. The method of claim 6, wherein the therapeutic agent is FVII.

9. The method of claim 1, wherein at least 50% of the lipidic particles have a size less than 140 nm.

10. The method of claim 9, wherein at least 60%, 70% 80% or 90% of the lipidic particles have a size less than 140 nm.

11. The method of claim 10, wherein at least 50%, 60%, 70%, 80% or 90% of the lipidic particles have a size between 40 to 100 nm.

12. The composition of claim 11, wherein the size of the lipidic particles is between 80 and 100 nm.

13. The method of claim 1, wherein the blood disorder is hemophilia.

14. The method of claim 1, wherein the compositions is administered via intravenous, intraperitoneal, mucosal, oral, subcutaneous, transdermal or intradermal route.

15. The method of claim 1, wherein the individual has developed antibodies to one or more proteins in the blood clotting cascade.

16. The method of claim 1, wherein the individual has developed antibodies to Factor VIII.

* * * * *

UNITED STATES PATENT AND TRADEMARK OFFICE
CERTIFICATE OF CORRECTION

PATENT NO. : 7,875,288 B2  
APPLICATION NO. : 11/731647  
DATED : January 25, 2011  
INVENTOR(S) : Balu-Iyer et al.

Page 1 of 1

It is certified that error appears in the above-identified patent and that said Letters Patent is hereby corrected as shown below:

Column 1, lines 10-13 should read:

--This invention was made with government support under Grant No. HL070227 awarded by the National Heart Lung and Blood Institute/National Institutes of Health. The Government has certain rights in the invention.--

Signed and Sealed this
Sixteenth Day of August, 2011

David J. Kappos
*Director of the United States Patent and Trademark Office*